United States Patent [19]

Takaya et al.

[11] 4,331,544

[45] May 25, 1982

[54] CATALYST FOR METHANATION AND METHOD FOR THE PREPARATION THEREOF

[75] Inventors: Haruo Takaya, Abiko; Tadasuke Hosoya, Chiba; Kiyoshi Ogawa, Yokohama; Shigemitsu Shin, Yatabe; Michio Araki; Kunio Suzuki, both of Sakura; Naoyuki Todo, Abiko, all of Japan

[73] Assignee: Director-General of the Agency of Industrial Science and Technology, Tokyo, Japan

[21] Appl. No.: 226,401

[22] Filed: Jan. 19, 1981

[30] Foreign Application Priority Data

Feb. 1, 1980 [JP] Japan .................................. 55-11734
Mar. 6, 1980 [JP] Japan .................................. 55-28877

[51] Int. Cl.$^3$ ............................................. B01J 23/84
[52] U.S. Cl. ..................................... 252/443; 585/733
[58] Field of Search ......................................... 252/443

[56] References Cited

U.S. PATENT DOCUMENTS 2,539,414  1/1951  Frankenburg ..................... 252/443
2,755,228  7/1956  Anhorn et al. ..................... 252/443

*Primary Examiner*—Arthur P. Demers
*Attorney, Agent, or Firm*—Brisebois & Kruger

[57] ABSTRACT

The invention provides a novel highly heat-resistant solid catalyst for the methanation of hydrogen and carbon monoxide into methane. Different from conventional nickel catalysts, the inventive catalyst comprises a binary active ingredient composed of an alloy of nickel and molybdenum and a molybdenum carbide supported on a porous catalyst carrier. The catalyst is prepared by heating a catalyst intermediate comprising the oxides of nickel and molybdenum supported on the carrier in a gaseous mixture of hydrogen and carbon monoxide at 500°–700° C., preferably, following a step of hydrogen reduction at 400°–900° C. The most preferable catalyst carrier is a mixture or a composite oxide compound composed of magnesium and aluminum oxides. The methanation reaction can be carried out with the inventive catalyst at a much higher temperature, e.g. 650° C., than with conventional catalysts so that the heat recovery from the gaseous product is greatly facilitated contributing to the energy economy.

10 Claims, 1 Drawing Figure

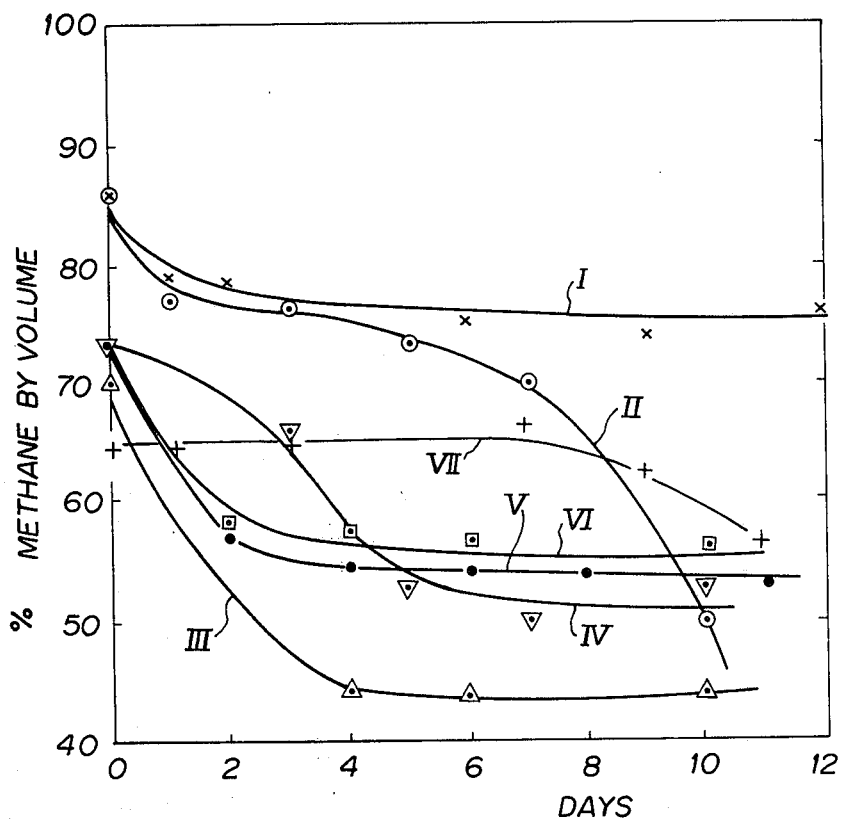

CATALYST FOR METHANATION AND METHOD FOR THE PREPARATION THEREOF

BACKGROUND OF THE INVENTION

The present invention relates to an improved catalyst for methanation and a method for the preparation thereof. More particularly, the invention relates to a catalyst for methanation having remarkably improved heat resistance and a method for the preparation thereof.

Methanation is a well known reaction by which methane is formed catalytically from hydrogen and carbon monoxide. This reaction is widely utilized for the production of high-caloric fuel gas mainly composed of methane from the so-called synthesis gas or water gas as a mixture mainly of hydrogen and carbon monoxide.

The reaction of methanation is an exothermic reaction evolving large quantities of heat of reaction amounting to 49 kilocalories per mole of the methane produced by the reaction. Therefore it is of imperative importance in the industrial practice of the methanation from the standpoint of energy economy of the process to effectively utilize the heat of reaction in so large a quantity as an energy source. Needless to say, it is desirable to carry out the reaction of methanation at a temperature as high as possible in order to enhance the efficiency of heat recovery and utilization thereof as an energy source. This desirable condition is realized only with a catalyst capable of exhibiting high activity, high selectivity and high durability even in use at elevated reaction temperatures over conventional.

Conventional catalysts for the methanation containing nickel as the active ingredient are in general satisfactory in respect of the activity and selectivity but not suitable for the high temperature reaction rapidly losing their activity when used at an elevated temperature.

Therefore, the methanation reaction by use of a conventional nickel catalyst must be performed with utmost care for the temperature control of the catalyst bed by continuously removing the heat of reaction to avoid excessive temperature elevation which may cause rapid deterioration of the catalyst activity. As a consequence, the efficiency in the recovery of the heat of reaction and the utilization thereof cannot be so high as desired. Various attempts have been made to develop a methanation catalyst having good heat resistance to be suitable for a high temperature reaction but without success.

SUMMARY OF THE INVENTION

Thus, the primary object of the present invention is to provide a means for enhancing the efficiency of heat recovery in the methanation, by which methane is produced in a high yield from hydrogen and carbon monoxide, by carrying out the reaction at a relatively high temperature.

Another object of the invention is to provide a novel and improved catalyst for the methanation reaction suitable for use in the reaction at a high temperature with markedly extended catalyst life.

A further object of the invention is to provide a method for the preparation of the above mentioned catalyst.

The solid catalyst for the high-temperature methanation according to the present invention and discovered by the inventors comprises (a) a porous catalyst carrier, preferably, containing a compound or a mixture composed of magnesium oxide and aluminum oxide, and (b) a binary active ingredient composed of an alloy of nickel and molybdenum and a molybdenum carbide supported on the porous catalyst carrier.

The method of the invention for the preparation of the above mentioned novel catalyst for methanation comprises the steps of (a) impregnating the porous catalyst carrier with a mixture or a composite oxide composed of a nickel oxide and a molybdenum oxide, and (b) heating the nickel/molybdenum supporting porous catalyst carrier in a gaseous mixture comprising hydrogen and carbon monoxide at a temperature within the range from 500° to 700° C.

The above mentioned step (b) is preferably preceded by a step of heating of the nickel/molybdenum supporting catalyst carrier in an atmosphere of hydrogen gas at a temperature within the range from 400° to 900° C.

BRIEF DESCRIPTION OF THE DRAWING

The FIGURE illustrates the decrease of the catalyst activity during the reaction at 650° C.

DETAILED DESCRIPTION OF THE PREFERRED EMBODIMENTS

It is a desirable characteristic in the methanation catalyst having high heat resistance as mentioned above that the catalyst, even after prolonged use in a high-temperature reaction, still retains a sufficiently high activity sufficient to restart the reaction at a relatively low temperature. This requirement of the activity exhibition at a relatively low temperature is readily understood when the necessity is taken into consideration that the reaction must be initiated when the reactant gases are introduced into a reactor column with thermal insulation at or in the vicinity of the entrance portion of the catalyst bed in the reactor. Once the reaction is commenced, the temperature of the catalyst bed is spontaneously increased by the heat of reaction produced in the exothermic methanation reaction so that the gaseous mixture readily reaches the equilibrium composition. The temperature of the gaseous product is determined as a function of the volumes of the hydrogen and the carbon monoxide having reacted and the temperature is equal to the temperature of the catalyst at or in the vicinity of the exit portion of the catalyst bed when the reactor column is thermally insulated. This means that the temperature of the gaseous reaction mixture cannot be higher than the highest temperature which the catalyst can withstand. Accordingly, in turn, the rate of conversion of the hydrogen and carbon monoxide to methane is limited by the range between the lowest temperature of the activity exhibition of the catalyst and the highest temperature to ensure sufficient durability of the catalyst activity leading to the limitation of the concentrations of these reactant gases in the gaseous feed.

As is mentioned before, the inventive catalyst contains a binary active ingredient composed of an alloy of nickel and molybdenum and molybdenum carbide supported on a porous catalyst carrier. The porous catalyst carrier is not particularly limited to specific ones and a variety of conventional oxide catalyst carriers may be used. For example, the main component of the catalyst carrier may be a single oxide selected from the group consisting of aluminum oxide, silicon dioxide, boron oxide, magnesium oxide, titanium dioxide, zirconium dioxide, lanthanum oxide and the like or a mixture as well as a composite oxide thereof such as silica-alumina, alumina-boria and the like.

Particularly recommended porous catalyst carrier, which should desirably have a specific surface area of at least 30 m$^2$/g, is at least partly composed of magnesium oxide and aluminum oxide either as a mixture thereof or as a composite oxide compound such as magnesium aluminate. In this case, preferred proportion of the magnesium oxide to the aluminum oxide is in the range from 5/95 to 40/60 or, more preferably, from 20/80 to 34/66 in the atomic ratio of Mg/Al and the content of the magnesium and aluminum oxide components in the carrier is preferably 50% by weight or more.

Such a composite oxide carrier of magnesium and aluminum can be prepared by the coprecipitation of magnesium and aluminum hydroxides from an aqueous solution containing water-soluble salts of these elements by the adjustment of the pH value with a suitable alkaline precipitant such as ammonium carbonate and ammonia water followed by calcination of the precipitates at 500° C. or higher.

The contents of the nickel and molybdenum active ingredients supported on the porous catalyst carrier are from 1 to 50% by weight or, preferably, from 3 to 30% by weight as NiO and from 1 to 40% by weight or, preferably, from 5 to 30% by weight as $MoO_3$.

The nickel component in the inventive catalyst is active in the state of an alloy with the molybdenum component. The alloy is composed, preferably, of 1–15 atomic % of Mo and 99–85 atomic % of Ni although the proportion depends on the equilibrium with the molybdenum carbide and is approximately at 10/90 of the Mo/Ni atomic ratio. The nickel-molybdenum alloy should be well blended with the particles of the molybdenum carbide or supported uniformly on the particles of the molybdenum carbide. This desirable state of the active ingredient is obtained by the specific preparation procedure of the catalyst according to the invention. In the intermediate stage of the catalyst preparation, it is a necessary condition that the nickel and the molybdenum components are present in the form of a composite oxide compound or in the form of an intimately blended mixture of the oxides supported on the porous catalyst carrier so as that the hydrogen reduction of the composite oxide compound or the oxide mixture produces an alloy or an intermetallic compound of nickel and molybdenum as an atomically dispersed intermixture of the elements. When the catalyst intermediate of the composite oxide compound or oxide mixture of nickel and molybdenum supported on the porous catalyst carrier is heated in an atmosphere of a gaseous mixture containing hydrogen and carbon monoxide under high pressure, a nickel-molybdenum alloy is formed by reduction as finely dispersed among the molybdenum carbide particles formed by the carbonization reaction to give a highly heat-resistant catalyst of the invention.

The procedure for the preparation of the inventive catalyst is not particularly different in its outline from conventional procedures for the preparation of similar catalysts. For example, the porous catalyst carrier is impregnated with thermally decomposable compounds of nickel and molybdenum followed by the thermal decomposition of them into oxide forms to give a catalyst intermediate containing a composite oxide compound or an oxide mixture of nickel and molybdenum supported on the carrier. The amount of impregnation of the carrier with the decomposable nickel and molybdenum compounds should be determined such that the finished catalyst contains each 1–50% by weight of the nickel-molybdenum alloy and the molybdenum carbide based on the weight of the carrier. The catalyst intermediate is then heated in an atmosphere of a gaseous mixture containing hydrogen and carbon monoxide at a temperature in the range from 500° to 700° C. under a superatmospheric pressure of at least 40 kg/cm$^2$ in order to avoid carbon deposition, if necessary, preceded by a heating treatment in a hydrogen atmosphere at 400° to 900° C. This preliminary treatment in hydrogen may be carried out under atmospheric pressure. The two-step treatment including the preliminary hydrogen treatment above is advantageous to give a well-controlled catalyst performance with good reproducibility. By the above heating treatment in the hydrogen-carbon monoxide gaseous mixture, optionally, with the preliminary treatment in hydrogen, reduction and carbonization of the oxides of nickel and molybdenum take place simultaneously to give the desired binary active ingredient composed of an alloy of nickel and molybdenum and a molybdenum carbide. The proportion of hydrogen and carbon monoxide in the gaseous mixture used for the reduction/carbonization treatment is preferably in the range from 75/25 to 95/5 by volume of the $H_2/CO$ ratio but it is a convenient way that the same gaseous mixture to be used in the subsequent methanation reaction, such as a synthesis gas, is used also in this treatment.

The molybdenum carbide produced by the carbonization is mostly $Mo_2C$ with a small amount of MoC as detected by the X-ray diffractometry although the proportion of $Mo_2C$ and MoC, which may be influenced by the types of the carrier or other parameters, has no particular influence on the catalyst performance.

In practicing the above treatment, the catalyst intermediate having the oxides of nickel and molybdenum supported on the carrier is packed into a reactor column through which the reactant gaseous mixture is passed at a temperature of 500° to 700° C. or, preferably, 620° to 680° C., if desired, following the preliminary treatment in pure hydrogen to effect the reduction and carbonization of the nickel and molybdenum components into the alloy and the carbide. The treatment is continued until the oxides of nickel and molybdenum are no longer detected by the X-ray diffractometry to show the formation of the alloy and the carbide. Usually, it takes about 5–15 hours.

The reaction of methanation by use of the inventive catalyst is carried out as a continuous process by passing a gaseous reactant mixture containing hydrogen and carbon monoxide through a reactor column filled with the catalyst forming either a fixed bed or a fluidized bed and kept at a temperature of 300° to 700° C. The pressure of the gaseous reactant mixture is preferably in the range from 50° to 100° kg/cm$^2$ and the space velocity is preferably not to exceed 50,000 per hour so as that the reaction equilibrium is well reached.

The composition of the gaseous reactant mixture is not particularly limitative and the so-called synthesis gas or water gas used for the production of methane by the methanation may be used as such. Usually the gaseous reactant mixture contains from 10 to 75% by volume of hydrogen and from 3 to 25% by volume of carbon monoxide. It is of course that the gaseous reactant mixture may contain certain lower hydrocarbons such as methane and ethane as the impurities.

Following is the example to illustrate the present invention in further detail.

EXAMPLE

Several kinds of porous catalyst carriers as indicated in Table 1 were prepared including a magnesium oxide-aluminum oxide carrier which was obtained by the coprecipitation of mixed hydroxides of magnesium and aluminum obtained by the coprecipitation from an aqueous solution containing magnesium and aluminum nitrates dissolved therein in an atomic ratio of ½ of Mg/Al by the addition of ammonia water as the precipitant followed by thorough washing of the precipitates with water and calcination at 500° C.

Each of the catalyst carriers was impregnated with the nickel and molybdenum components using nickel nitrate and ammonium paramolybdate as the starting materials for the components by the blending method. The contents of the nickel and molybdenum components in the catalyst carrier thus impregnated with the components were such that the weight ratio of NiO:-MoO$_3$:carrier was 20:25:55.

A reactor column of 12 mm diameter was filled with 2 ml of the above prepared catalyst precursor and hydrogen gas was passed through the column kept at 700° C. for about 15 hours under atmospheric pressure. Thereafter, a gaseous reactant mixture composed of 45%, 15% and 40% by volume of hydrogen, carbon monoxide and methane, respectively, was passed through the column at 650° C. for about 15 hours with pressurization to 80 kg/cm$^2$. Extension of the treatment time over 15 hours gave no particular additional advantages.

The catalyst thus obtained was examined by the X-ray diffractometry to find that the oxides of nickel and molybdenum had disappeared and an alloy of nickel and molybdenum and a molybdenum carbide were formed.

A continuous run of the methanation reaction was undertaken with the reactor column filled with the above prepared catalyst at the same temperature and under the same pressure by passing the same gaseous reactant mixture therethrough as in the catalyst preparation in a space velocity of 15,000 per hour.

In the above described continued run carried out at 650° C., the temperature of the reactor column was periodically lowered to 400° C., the other parameters being maintained as unaltered, and the gaseous product mixture was analyzed for the content of methane so as that the difference in the catalyst activity between different catalysts could be better distinguished than at 650° C. Meanwile, the equilibrium content of methane in the gaseous product was about 80% by volume at 650° C. and about 96% by volume at 400° C. Table 1 summarizes the results obtained at the last day of the continued run for each of the catalyst carriers together with the initial value directly after the catalyst preparation.

TABLE 1

| Run No. | Catalyst carrier | Specific surface area, m$^2$/g | Methane content in the product gas at 400° C. as a measure of catalyst activity, % by volume | |
|---|---|---|---|---|
| | | | Initial | After days of reaction at 650° C. |
| I | Magnesia-alumina, calcined at 500° C. | 120 | 86% | 75% after 12 days |
| II | Alumina, calcined at 1000° C. | 40 | 86% | 50% after 10 days |
| III | Alumina, calcined at 500° C. | 140 | 70% | 44% after 10 days |
| IV | Hydrated alumina | 160 | 73% | 53% after 10 days |
| V | Silica sol No. 1*[1] | 80 | 73% | 53% after 11 days |
| VI | Silica sol No. 2*[2] | 100 | 73% | 56% after 10 days |

*[1]Commercial product by Shokubai Kasei Co.
*[2]Commercial product by Nippon Kasei Co.

The activity data obtained in the above runs I to VI are also plotted in the accompanying FIGURE taking the days of the reaction as the abscissa and the content of methane in the gaseous product as the ordinate, in which Curves I to VI are for the runs I to VI, respectively.

For comparison, the same alumina carrier as used in the above run No. II was impregnated with the nickel ingredient alone omitting the molybdenum ingredient in a supporting amount of 15% by weight as NiO and treated with the same gaseous reactant mixture at 500° C. for about 15 hours under a pressure of 80 kg/cm$^2$.

The activity of this nickel catalyst was sufficiently high directly after preparation to give a methane content of 82% by volume at 400° C. in the gaseous reaction product. This catalyst was, however, poorly heat-resistant and had been completely deactivated after 24 hours of the continued run at 650° C. Meanwhile, the reduction treatment of the catalyst in hydrogen instead of the treatment with the gaseous reaction mixture gave substantially the same results.

For further comparison, a commercially available nickel catalyst for methanation was subjected to the same reduction/carbonization treatment as in the above except that the temperature in the preliminary hydrogen treatment was 400° C. instead of 700° C. The X-ray diffractometry of the thus treated catalyst indicated that the nickel constituent had been converted to metallic. This catalyst was used in a continuous run of the methanation reaction under the same conditions as in the runs with the inventive nickel-molybdenum catalysts to give a result that the catalyst activity was very low even at the initial stage directly after the reduction/carbonization treatment at 650° C. reaching 42% by volume of the methane content at 400° C. after 24 hours of the continued run. This result indicated that that catalyst activity was almost completely lost in consideration of the methane content of 40% by volume in the gaseous feed by the reaction at 650° C. even though the activity of this catalyst was sufficiently high when tested at 400° C. directly after the hydrogen reduction at 400° C. to give a methane content of 97% by volume in the gaseous product.

The effect of the hydrogen treatment is illustrated by the activity data of Curve VII in the FIGURE obtained by the omission of the hydrogen treatment in Run No. 1 where the mixed gas was directly passed with a space velocity of 3000 per hour under 86 kg/cm$^2$ first at 500° C. and then continuously at 400° C.

What is claimed is:

1. A solid catalyst for the synthesis of methane from hydrogen and carbon monoxide which comprises
   (a) a porous catalyst carrier, and
   (b) a binary active ingredient composed of an alloy of nickel and molybdenum and a molybdenum carbide supported on the porous catalyst carrier.

2. A method for the preparation of a solid catalyst for the synthesis of methane from hydrogen and carbon monoxide which comprises the steps of
   (a) impregnating a porous catalyst carrier with a mixture or a composite oxide compound composed of a nickel oxide and a molybdenum oxide to give a catalyst intermediate, and
   (b) heating the catalyst intermediate in an atmosphere of a gaseous mixture comprising hydrogen and carbon monoxide at a temperature in the range from 500° to 700° C. to convert the nickel and molybdenum ingredients to a binary active ingredient composed of an alloy of nickel and molybdenum and a molybdenum carbide supported on the porous catalyst carrier.

3. A method for the preparation of a solid catalyst for the synthesis of methane from hydrogen and carbon monoxide which comprises the steps of
   (a) impregnating a porous catalyst carrier with a mixture or a composite oxide compound composed of a nickel oxide and a molybdenum oxide to give a catalyst intermediate,
   (b) heating the catalyst intermediate in an atmosphere of hydrogen gas at a temperature in the range from 400° to 700° C. to reduce the oxides of nickel and molybdenum into metallic states, and
   (c) heating the catalyst intermediate bearing the nickel and molybdenum ingredients reduced to the metallic states in an atmosphere of a gaseous mixture comprising hydrogen and carbon monoxide at a temperature in the range from 500° to 700° C. to convert the nickel and molybdenum ingredients to a binary active ingredient composed of an alloy of nickel and molybdenum and a molybdenum carbide supported on the porous catalyst carrier.

4. The solid catalyst as claimed in claim 1 wherein the porous catalyst carrier comprises an oxide, a mixture of oxides or a composite oxide compound composed of the oxides selected from the group consisting of aluminum oxide, silicon dioxide, boron oxide, magnesium oxide, titanium dioxide, zirconium dioxide and lanthanum oxide.

5. The solid catalyst as claimed in claim 4 wherein the porous catalyst carrier contains at least 50% by weight of a mixture of magnesium oxide and aluminum oxide or a composite oxide compound composed of magnesium oxide and aluminum oxide.

6. The solid catalyst as claimed in claim 5 wherein the porous catalyst carrier contains magnesium oxide and aluminum oxide in amounts such that the atomic ratio of magnesium to aluminum is in the range from 5:95 to 40:60.

7. The method as claimed in claim 2 wherein the step (b) is conducted in an atmosphere under a pressure of at least 40 kg/cm$^2$.

8. The method as claimed in claim 3 wherein the step (c) is conducted in an atmosphere under a pressure of at least 40 kg/cm$^2$.

9. The method as claimed in claim 2 or claim 3 wherein the atmosphere comprising hydrogen and carbon monoxide contains hydrogen and carbon monoxide in a volume ratio in the range from 75:25 to 95:5.

10. The solid catalyst as claimed in claim 1 containing nickel and molybdenum in amounts of from 1 to 50% by weight as NiO and from 1 to 40% by weight as MoO$_3$, respectively.

* * * * *